United States Patent [19]
Melvin et al.

[11] Patent Number: 6,032,076
[45] Date of Patent: Feb. 29, 2000

[54] TRANSINTEGUMENTAL POWER TRANSFORMERS WITH HIGH PERMEABILITY CORES

[75] Inventors: David Melvin; H. Thurman Henderson; Arthur J. Helmicki, all of Cincinnati, Ohio

[73] Assignee: The University of Cincinnati, Cincinnati, Ohio

[21] Appl. No.: 09/045,432

[22] Filed: Mar. 20, 1998

Related U.S. Application Data

[60] Provisional application No. 60/041,330, Mar. 20, 1997.

[51] Int. Cl.$^7$ ........................................................ A61N 1/00
[52] U.S. Cl. .................................................. 607/61; 607/1
[58] Field of Search .............................. 623/3; 607/1, 2, 607/65, 61

[56] References Cited

U.S. PATENT DOCUMENTS

| | | |
|---|---|---|
| 3,731,669 | 5/1973 | Fitzgerald . |
| 4,056,097 | 11/1977 | Maass . |
| 4,143,661 | 3/1979 | LaForge et al. . |
| 4,432,363 | 2/1984 | Kakegawa . |
| 4,800,901 | 1/1989 | Rosenberg . |
| 4,895,150 | 1/1990 | Isaacson et al. . |
| 5,109,843 | 5/1992 | Melvin et al. . |

OTHER PUBLICATIONS

Toshi Hiro Nisimura et al., A Large Air Gap Flat Transformer for a Transcutaneous Energy Transmission System, 25th IEEE Power Electronics Specialists Conference 1994.

Ahn, Jae Mok et al., In Vivo Performance Evaluation of a Transcutaneous Energy and Information Transmission System for the Total Artificial Heart, ASAIO Journal, 1993, p. 208–212.

Matsuki, Hidetoshi, et al., Simulations of Temperature Rise on Transcutaneous Energy Transmission by Non–contact Energy Transmitting Coils, IEEE Transactions on Magnetics, vol. 29, No. 6. Nov. 1993, p. 3334–6.

Melvin, David B., et al., Electric Power Induction Through an Isolated Intestinal Pouch, Trans. Am. Soc. Artif. Intern. Organs, vol. 37, 1991, p. M203–4.

Melvin, D.B., et al., Design Modifications to an Enteric Pouch Transformer, Int. J. Art. Organs, 1991: 14, 572.

Mussivand, Tofy, et al., Transcutaneous Energy Transfer System Performance Evaluation, Artifical Organs 17(11): 1993, p. 940–947.

Myers, George H., et al. , A Transcutaneous Power Transformer, Trans. Amer. Soc. Artif. Int. Organs, vol. 14, 1968, p. 210–214.

Newgard, P., et al., Skin Transformer and Power Conditioning Components, Proceedings of the First Artificial Heart Program Conference, Jun. 1969, p. 927–936.

(List continued on next page.)

*Primary Examiner*—Scott M. Getzow
*Attorney, Agent, or Firm*—Wood, Herron & Evans, LLP

[57] ABSTRACT

Extra- to intra-corporeal power is provided by a transformer implanted at least partially within a defunctionalized intestinal pouch (or sack), such as an ileal pouch. The transformer includes a continuous loop magnetic core which is implanted within the pouch. The pouch itself includes a passageway permitting the secondary wiring to extend around the and through the magnetic core and through its central opening without entering the pouch providing intra-corporeal current. Wire providing the primary windings extend from outside the body in through a stoma into the pouch and surround portions of the magnetic core within the pouch. Because of the use of a generally continuous loop magnetic core of high permeability, there is little or virtually no magnetic flux leakage. A solid circular core of a high permeability material may be used. In an alternate embodiment of the present invention the magnetic core can be divided into two separate portions, one implanted within the pouch and one implanted within the peritoneum adjacent the pouch so that the two core portions combine to form a generally continuous loop magnetic path, separated only by the intestinal wall of the pouch.

18 Claims, 3 Drawing Sheets

OTHER PUBLICATIONS

Rangan, V., et al., Non–Linear Robust Control of a Series Resonant DC/DC Converter for Bio–Medical Applications, 1996 IEEE Conference on Control Applications, Dearborn, MI, Sep. 1996.

Schmidt, C. H., et al., A Transcutaneous Energy Transmission System for Rotary Blood Pumps, Proc. of Int. Workshop on Rotary Blood Pumps, Vienna 1991, p. 77–81.

Schuder, John C., Energy Transfer into a Closed Chest by Means of Stationary Coupling Coils and a Portable High–Power Oscillator, Trans. of Assoc. for Soc. Artif. Internal Organs; 7, 1961, p. 327–329.

Sherman, C., et al., Energy Transmission Across Intact Skin for Powering Artificial Internal Organs, Trans. Am. Soc. Artif. Intern. Organs, v. 27, 1981, p. 137–9.

Andren, Carl F. et al., The Skin Tunnel Transformer: A New System that Permits Both High Efficiency Transfer of Power and Telemetry of Data Through the Intact Skin, IEEE Transactions on Bio–Medical Engineering, vol. BME–15, No. 4, Oct. 1968, p. 278–280.

Snyder, Alan J., et al., In Vivo Testing of a Completely Implanted Total Artificial Heart System, ASAIO Journal 1993, p. M177–184.

Takatani, Setsuo, et al., Totally Implantable Total Artificial Heart and Ventricular Assist Device with Multipurpose Miniature Electromechanical Energy System, Artificial Organs, 18(1), 1994, p. 80–92.

Bergeron, M.D., Patrice et al., Secondary Aortoduodenal Fistuals: Value of Initial Axillofemoral Bypass, Annals of Vascular Surgery, vol. 5, No. 1, 1991, p. 4–7.

Crookes, M.D., Peter F. et al., The Angelchik Prosthesis: What Have We Learned in Fifteen Years?, Ann. Thorac. Surg. 1994; 57:1385–6.

Dasse, Kurt A., et al., Biological Consequences of Chronic Transcutaneous Energy Transmission, Progress in Artificial Organs 1985; ISAO Press Cleveland 1986, p. 1127.

Ghahary, Ali, et al., Design of a Transcutaneous Energy Transmission System Using a Series Resonant Converter, IEEE Transactions on Power Electronics, vol. 7, No. 2., Apr. 1992, p. 261–269.

Helmicki, Arthur J., et al., Development of a High Permeability Cored Transintegumental Power Transformer, ASAIO Journal, 1996.

Himley, S.C., et al., Development of the E4T Electrohydraulic Total Artificial Heart, ASAIO Transactions, 36:M234–237, 1990.

LaForge, D.H., et al., The Belt Skin Transformer for Energy Transmission to Implanted Circulatory Support Devices, Artificial Organs, Proc. Int. Symp. on Artif. Organs., Biomed. Eng. and Transplantation, Ed. J.D. Andrade, VCH publ. pp. 95–107, 1987.

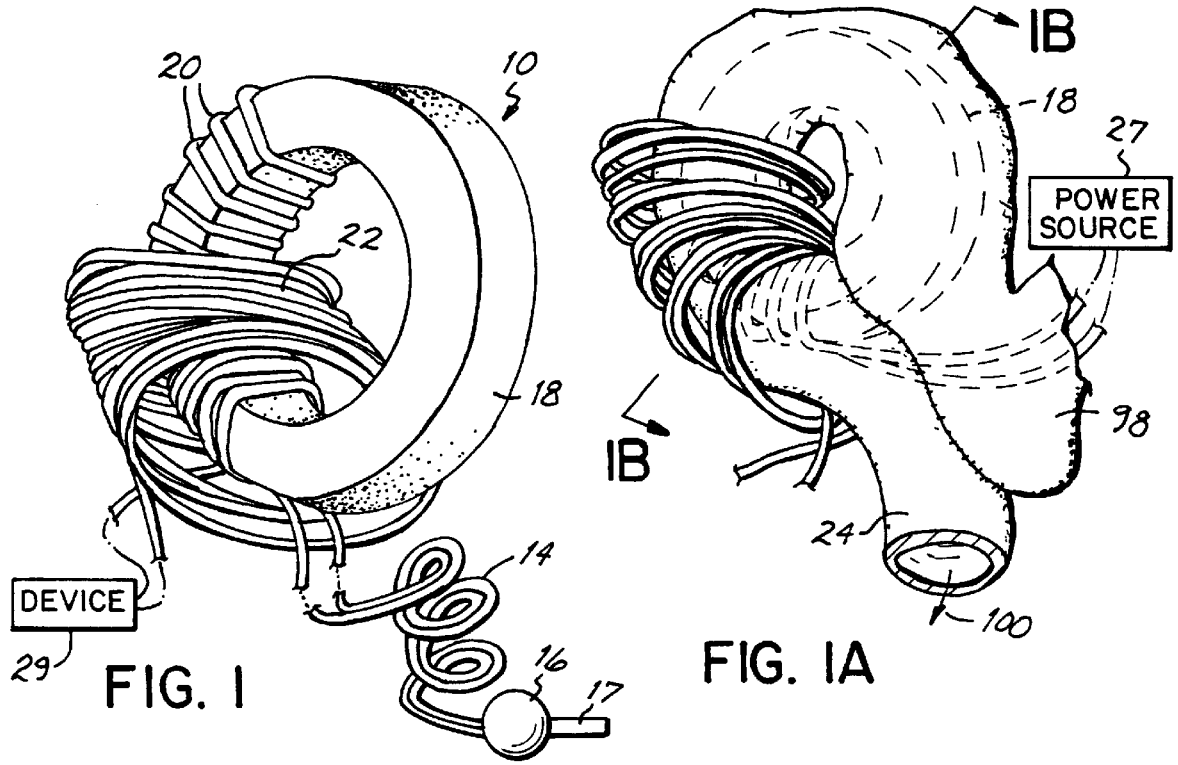
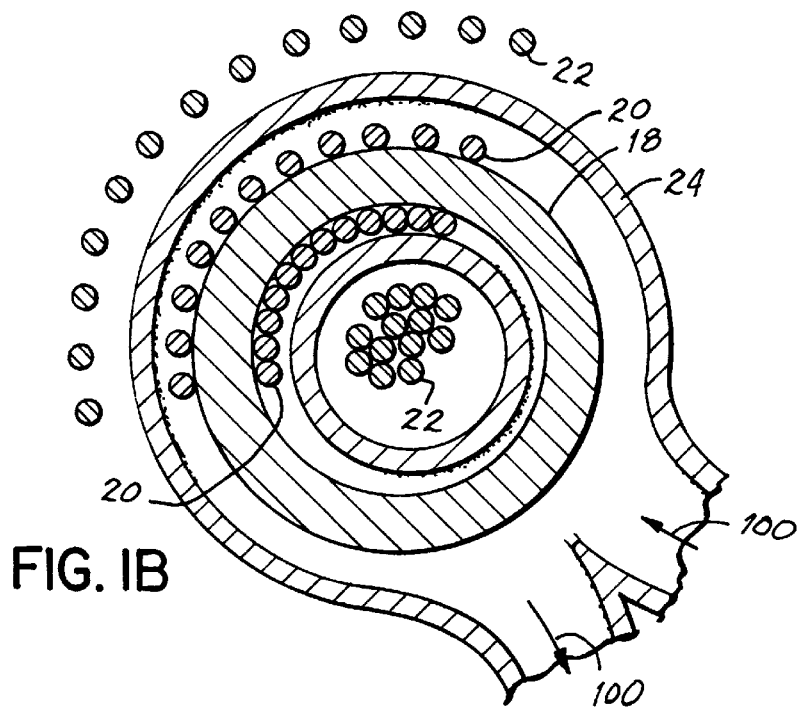

TRANSINTEGUMENTAL POWER TRANSFORMERS WITH HIGH PERMEABILITY CORES

RELATED APPLICATIONS

This application claims priority to U.S. provisional patent application Serial No. 60/041,330 filed Mar. 20, 1997, and entitled Transintegumental Power Transformers with High Permeability Cores, which is incorporated herein by reference in its entirety.

FIELD OF THE INVENTION

The present invention relates to transintegumental power transformers. Specifically, the present invention relates to transintegumental power transformers for use in powering and/or communicating with implantable prosthetic devices.

BACKGROUND OF THE INVENTION

There are a number of internal power consuming prosthetic devices now employed or contemplated for implantation in the human body. A common problem with all of these devices is providing an effective, safe power supply. Smaller devices such as pacemakers can use replaceable batteries. The necessity of surgically replacing such batteries periodically is not a significant problem. With respect to devices requiring more power than the pacemaker, battery-supplied power is inadequate. For example, devices such as artificial hearts require up to 20 watts of continuous power. A battery designed to provide such power for 60 days would be very large. Nuclear power supplies are also inappropriate since the shielding requirements would make these unsuitable. Further, if the shielding failed, the results could be detrimental to the user's health.

All devices used in humans for mechanical circulatory assistance have, therefore, required a permanent opening in the skin for energy transfer. These include pneumatic conduits for balloon pumps, the Jarvik total artificial heart, blood conduits for the Thoratec (Pierce Donachy) and Abiomed sacular pumps, an electrical cable for the Novacor solenoid pump, the Thermo Cardio Systems, Inc. (TCI) assist device, and a spinning torque cable for the Nimbus Hemo pump intravascular turbine. Whereas these have occasionally been used for extended periods of time without infection (over two years in one Jarvik patient and over one year in current Novacor, Thoratec and TCI recipients), clinical and experimental observations indicate that such an integumental break presents a continuing risk of infection.

Principally for this reason, none of these devices except the Jarvik have been seriously proposed for long term circulatory support. All the others have been promoted as strictly temporary aids for use during expected cardiac recovery or during the waiting period for a transplant donor. Infections have been minimal for these short periods.

Electrical induction has long been entertained as a means of delivering power from extra corporeal source across intact integument. In 1961, a transformer operating with radio frequency alternating current from an external to a subcutaneous coil was reported by Schuder, Stephenson and Townsend. It was reasoned that a coil within a coil configuration could be more efficient and a tube pedicled skin nap was utilized. Within this tube of skin (shaped like a suitcase handle and attached to the chest wall at either end) lay a secondary coil while the primary coil with an iron core (allowing a lower frequency current to be used), surrounded it. Efficiencies of 97% (57 watts, 20 kHz) were reported.

Two groups of investigators have pursued these concepts for the past decade and have been developing inductive energy transmission systems seriously intended for powering of clinical circulatory assist devices. A belt skin transformer was developed by LaForge at Novacor which consists of a narrow single turn flexible secondary coil implanted in the subcutaneous tissue around the waist and a five turn extra corporeal primary coil worn in a belt. This has effectively transmitted 15 watts of continuous power at more than 75% efficiency in both in vitro models and experimental animal models. This system is intended to be coupled with a modified version of Novacor's current temporary solenoid operated intra corporeal left ventricular assist system to form a support system for long term use. Animals with the implanted device have survived for over two years with little difficulty reported.

An induction device has been developed by Thermedics Inc. (now TCI) which is situated in and on the anterior abdominal wall. The implanted secondary coil is made of 16 turns of braided copper wire wrapped around a dome-shaped polyurethane appliance within the abdominal subcutaneous tissue. The primary is a 3 turn coil in a ring that is worn surrounding the mound produced by the secondary appliance and secured by a belt. Transmission of 24 watts has been demonstrated. In efficiency studies in animals this has delivered 6 to 12 watts of usable power with a 3 wall loss (65%–70% efficiency). Most of the losses were demonstrated in external components and about 1 watt was lost in the transformer itself, presumably as heat. A clinical form of this device is to be used with an electric version of Thermo Medical System's current pneumatic left ventricular assist system. These devices seem likely to offer a practical means for extra- to intra-corporeal energy transfer. Consideration of their use in patients, however, suggests some possible problems.

The only known prior use of a life supporting device that had to be maintained in the surface position was the radio frequency induction coil used in pacemakers before introduction of satisfactory implantable batteries. These worked very well electrically (the very low power requirements of pacemakers needed a much less efficient inductor than assist devices) but there was a high fatality rate clinically due to inadvertent displacement by the patient. Further changes in electrical load of a pumping device or minor component failure in the activating circuit can potentially increase the heat produced in implanted secondary coils. Potential for dissipation of this heat without damage to surrounding tissue is limited by tissue blood supply. A serious burn of the tissue layer separating the primary and secondary coils could lead to device infection. Further, the discomfort and annoyance of a device that the patient can constantly feel in contact with his or her skin compounded by the psychological impact of knowing that the itch, tickle, or irritation is to be there for life, is impossible to anticipate or calculate.

Treating heart failure mechanically requires power. While the net mechanical energy to pump five liters blood per minute at 100 mmHg incremental pressure, a typical requirement for an adult human at rest, is just 1.10 Watt [5 L/min * 100 mmHg * (0.001 $m^3$/L) * 1 min/60 s * (133 {$N/m^2$}/1 mmHg) * 1 W/(1 Nm/s)=1.10 W], desired reserve capacity and achievable efficiency make a supply of 10 to 20 watts preferable for either total artificial hearts or ventricular assist devices. Although internal sources (nuclear cells, chemical batteries, chemical fuel cells or harnessed skeletal muscles) are attractive, each has limitations not yet resolved. External power remains a requirement for devices doing most or all of the circulatory work. That power has been delivered in many ways.

Whether pneumatic tubes, hydraulic tubes, electric wires, or sheathed torque cables, direct connections are simple, reliable, and mechanically secure. Their limitation is that they may also be routes for infection of implanted hardware and contiguous tissue. Although meticulous entry site care and careful cable design have reduced this risk for some systems to a point that is perhaps tolerable for the time spent awaiting a heart transplant donor, some driveline infections still occur with systemic consequences (*J. Heart and Long Transpl.* 15:S73, 1996). Further, this experience is in a very controlled, usually in-hospital environment. Extending this protection to the five year, ten year, or longer survival likely needed to make "permanent" circulatory support a seriously acceptable offering, especially in a more relaxed, "normal" lifestyle and environment, may be a severe challenge. The somewhat analogous home maintenance of externalized dialysis shunts has succeeded in brief applications, but these have only rarely remained totally infection-free for many years in outpatients. An artificial heart line cannot be so simply removed and inserted elsewhere while eradicating episodic sepsis. External lines are one, though not the only, potential source of intrathoracic blood pump infections, and the prognosis of these infections is not good (*J. Cardiovasc. and Thor Surg.* 98:506–9, 1989). We believe this justifies continued interest in energy transmission through intact integument.

As discussed above, electrical induction has been considered by many investigators to be a reasonable means for doing this. Schuder, Stephenson, and Townsend (*Trans. Society Artificial Internal Organs* 1961;7:327–329) in 1961 reported air-core transformers operating with radio frequency current from an external to a subcutaneous coil. Both Andren, et al. (*The Institute of Electrical and Electronics Engineers: Trans. of Biomed. Eng.* 1968; 15: 278–280) and Newgard et al. (Hegyeli R., ed. *Proceedings of the First Artificial Heart Program Conference.* Washington, DC: US Government Printing Office, 1969:927–936) reasoned that a coil-within-a-coil concentric configuration could be more efficient and reported devices using a tube-pedicled skin flap. Within this tube of skin attached to the chest wall at either end lay a secondary coil, while the primary coil and an iron core (allowing use of lower frequency power) surrounded it. Myers et al. reported external and subcutaneous coils, each with a ferrite core giving total weight of 16 ounces and working at low audio frequencies (*Trans. Am. Soc. Artificial Internal Organs* 1968;14: 210–214). Other investigators have continued to pursue and develop these concepts. LaForge and colleagues at Novacor, Inc. (now Novacor Division of Baxter Healthcare Corp.) have developed a 400 to 600 kHz "belt skin transformer." (In: Andrade, J. D., ed. *Proceedings of the Internation Symposium on Artificial Organs, Biomedical Engineering and Transplantation.* New York: VCH Publishers, 1987: 95–107). This consists of a narrow single-turn flexible secondary coil implanted in the subcutaneous tissue around the waist and a five-turn extra corporeal primary coil worn in a belt. This has effectively transmitted 15 watts of continuous power at more than 75% total system efficiency in both in vitro and experimental animal models. The system is intended to be coupled with a modified version of Novacor's solenoid-operated intra corporeal left ventricular assist system for long-term support. A clinical system will include both external and internal storage batteries. Sherman, Dasse, and associates at Thermedics, Inc. (Thermo Cardiosystems, Inc., TCI) have developed a 180 kHz induction device to be placed in and on the anterior abdominal wall (*Trans. Society Artif. Internal Organs* 1981;27: 137–139). The implanted secondary coil is 16 turns of braided copper wire in a dome-shaped polyurethane appliance within the abdominal wall. Lying on the skin around the mound produced by the secondary is a ring containing a 3 turn primary. It has transmitted up to 24 watts of power. In chronic animal studies, it delivered 6 to 12 watts of usable power with 3 watts total loss and about 1 watt loss in the coils themselves (65% to 70% total system and about 90% coil-to-coil efficiency). This is intended to power the electric TCI intra corporeal left ventricular assist device.

A number of other devices share this external primary ring and subcutaneous secondary cone coil arrangement. That arrangement was developed by Schima and associates at the University of Vienna functions at a considerably higher frequency (1.0 MHZ), permitting greater freedom of displacement with satisfactory maintenance of coupling (*Proceedings of the International Workshop on Rotary Blood Pumps.* Vienna 1991: 77–81). The Ottawa group uses an "autotuned" system in which frequency varies in the 400 to 500 kHz range depending on coil separation (*Artif. Org.* 17:940–7, 1993) while the Penn State system operates at 160 kHz (*ASAIO Journal.* 39:M177–84, 1993). Other recently described devices operate at 210 kHz (*Artificial Organs* 18: 80–92,1994), 230 kHz (*IEEE Transaction on Magnetics.* 29:3334–6, 1993),240 kHz (*ASAIO Journal* 39:M208–12, 1993). Most of these have dome-shaped implanted secondary appliances with thicknesses of 1.5 to 3 cm and diameters similar to the 7.1 cm of Penn State or the 6.6 cm of the Ottawa device. The secondary appliance described by Ahn et al. is notably smaller, only 3.8 cm in diameter. Primary rings are usually 2 to 3 cm greater in diameter than secondary ones.

Most of these transformer devices function well, in that they have been shown to effectively transfer sufficient energy to supply expected needs for practical electric artificial hearts and assist devices. They may well afford more lifestyle freedom than do the care regimens mandated by skin-penetrating, direct connection lines, even if the safety of such regimens were to be demonstrated for indefinite periods. This assumes that neither maintenance of alignment, tissue warming, nor magnetic flux leakage become serious clinical problems. The constant tissue warming, while causing problems in early prototypes of at least one device, exceeded surrounding tissue by only 1.6 to 2.5° C. in others and, for some sort of physical position maintenance (other than the brief grade periods granted by internal batters) may be annoying, but not likely tolerable.

Melvin, U.S. Pat. No. 5,109,843, discloses the first extra-to intra-corporeal power supply positioned within a defunctionalized intestinal pouch. Specifically, an ileal pouch is used. The disclosure of this reference is incorporated herein by reference in its entirety. This employs a single cylindrical or bulbous ferrite core with primary wrappings around the core in the pouch. Secondary windings extend around the outside of the pouch, i.e. within the body. Due to the design and construction of the ferrite core, it suffers from significant magnetic flux leakage.

Magnetic flux leakage may impose significant lifestyle restrictions of its own. Air-core power transformers operating at the radio frequencies required for reasonable coupling also generate substantial flux fields well beyond the subject's body. That invites interference, both to external electronic devices and from contiguous metal and magnetic materials. Interference with electronic devices might be only a nuisance, though considering the power levels involved and the ubiquity of such devices in most people's lives, it could be a major nuisance. Interference to the device from contiguous magnetic or even nonmagnetic metal could be far more serious. This was tested in only one of the publications reviewed. The Ottawa device showed a 10% attenuation of function with a "metal object" (mass and type of metal not given) in contact with the primary coil. Rigorous testing with progressively more massive metal of varying magnetic permeabilities has not been reported. The consequence of the hospital-liberated, device-dependent person resting upon or leaning against all manner of common metal structures, some quite massive and of both magnetic and non-magnetic metals, is an open question. There are at least theoretical grounds to expect, in the absence of absolutely perfect coil alignment, that such everyday activities as sitting in wrought iron chairs, leaning on structural steel pillars or car doors, and walking by fire hydrants or bank safes may not be innocuous. Some degree of transmitted power attenuation might be addressed by compensatory design adjustments; a battery-draining near short-circuit through the contiguous metal could be far more serious. For a technology whose rationale is largely based on safely extending its recipients' range of activities and environments, this is no small concern. Clearly, safety testing to quantify or disprove such risks is indicated.

SUMMARY OF THE INVENTION

The present invention is premised upon the realization that one can form a transintegumental transformer virtually free of magnetic flux leakage i.e., less than the order of magnitude beyond the earth's magnetic field, by establishing a complete or near-complete magnetic circuit with high permeability core material. The transintegumental transformer of the present invention employs a continuous magnetic loop or generally continuous magnetic loop using a magnetic core with high permeability which is implanted within the body. Either all or a portion of the core is located within an intestinal pouch with the wiring for the primary winding extending through a miniature stoma into the pouch. In one embodiment, an ileal pouch is used. The secondary winding of the transformer is within the body and surrounds the walls of the pouch. The wires are then directed to an implanted electrical device.

When the core material is a solid or complete circular core material, the core is totally enclosed within the pouch and the pouch is torroidal, having a central opening which permits the secondary winding to wrap around and through the center of the core without passing through the wall of the pouch.

When the core is not complete, but is separated into two portions, a portion of the core material is located within the pouch with the primary windings extending around it. The second portion of the magnetic core is attached to the exterior surface with the secondary windings extending around the second portion of the magnetic core. Together these portions form a generally continuous magnetic loop. This significantly reduces or eliminates the magnetic flux leakage encountered and permits the user to experience any typical environment without significant power loss.

The objects and advantages of the present invention will be further appreciated in light of the detailed descriptions and drawings in which captions brief descriptions of the figures.

BRIEF DESCRIPTION OF THE DRAWINGS

The accompanying drawings, which are incorporated in and constitute a part of this specification, illustrate embodiments of the invention and, together with a general description of the invention given below, serve to explain the principles of the invention.

FIG. 1 is a perspective view of one embodiment of the present invention with the intestinal pouch removed.

FIG. 1A is a perspective view of the embodiment shown in FIG. 1 with the intestinal pouch present.

FIG. 1B is a diagrammatic cross-sectional view of the transformer of the present invention positioned in an intestinal pouch.

DETAILED DESCRIPTION

Figures 7A, 7B:
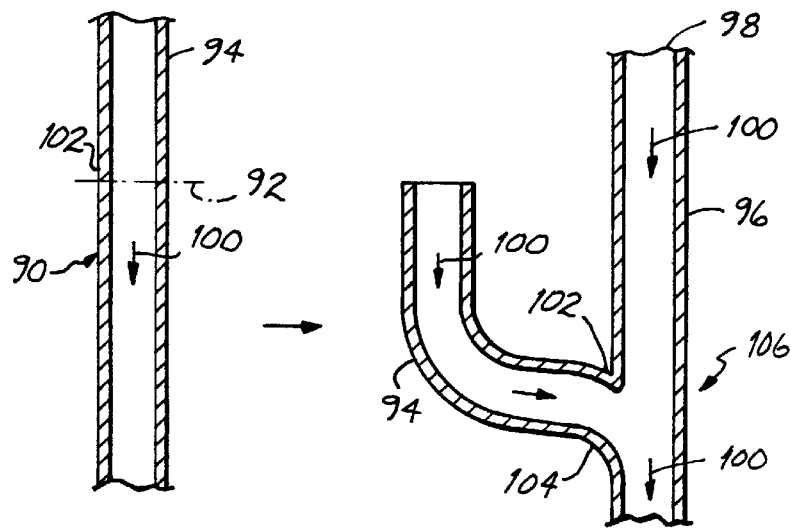
FIG. 7A and 7B are diagrammatic depictions of the intestines and a Roux-Y segment.

Alternative embodiments of the invention are illustrated in the figures and share some common components. Referring to FIGS. 1, 1A, and 1B, a transformer device 10 (Embodiment 1) is shown, whereas in FIGS. 2A and 2B, an alternative transformer device 12 (Embodiment 2) is illustrated.

Insofar as design differences allow, some similar materials and techniques are used for the two transformer device embodiments 10, 12. For their primary and secondary wire windings, both embodiments use 38/100 SPSN braided Litz wire (18 ga. equivalent, available from Cooner Corp., Chatsworth, Calif.). The leads to the various windings and to the devices are coaxial cables 17 such as an AS298 medical grade silicone insulated silver-plated, copper-braided central conductor inside a NEQ 24736 TC braided tinned copper sheath, also available from Cooner Corp. Primary appliances coupled to each of the transformer devices 10, 12 will be isolated from possible external lead traction by interposing a double helix of wire 14 (see FIG. 1 ) and a retaining 1.2 cm silicone sphere 16 at the junction of lead wire 14 and coaxial cable 17. One such suitable sphere is made of 1300T silicone available from Shinetzu Chemical Co., Ltd., Tokyo, Japan. All cables and wires used for the transformer devices 10, 12 are individually clad with snugly fitting silicone rubber tubing available from Silastic, Dow-Corning, Midland, Mich. The cores of the devices 10, 12 and their fixed primary windings are encased in nylon mesh impregnated with silicone rubber such as Silicone Adhesive, from Dow-Corning, Midland, Mich. The transformer devices 10, 12 of the invention provide suitable operating characteristics and material properties, and address the biological constraints in size, shape and capacity, to minimize power losses.

Figure 3:
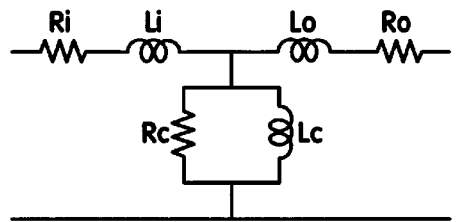
FIG. 3 is an electrical equivalent in schematic of the transformer or the invention.

FIG. 3 shows a schematic circuit diagram which is an equivalent circuit model for the transformer devices 10, 12 of the invention. The symbols $R_i$ and $L_i$ are used to denote the input resistance and self-inductance, respectively, on the primary side of the device. The components $R_o$ and $L_o$ denote the output resistance and self-inductance, respectively, on the secondary side of the device. The components $R_c$ and $L_c$ denote the equivalent core resistance and mutual inductance, respectively, with respect to the core material. It is desirable to minimize the various resistance values $R_i$, $R_o$, and $R_c$ and to maximize the core inductance $L_c$ for operation of the invention.

Embodiment 1

FIGS. 1, 1A, and 1B illustrate perspective and cross-sectional views of the device 10 of the invention, as coupled into a circular intestinal pouch. In one embodiment of the invention as disclosed herein, the pouch is an ileal pouch. However, other portions of the intestine might be used to form the intestinal pouch. Device 10 includes a high permeability magnetic core 18, such as a core made from wound 0.5 mil thick magnetic tape (Square Permalloy, from Magnetics, Inc. Butler, Pa.). Core 18 is generally circular and, in accordance with one aspect of the invention, is a solid or continuous circular structure to form a continuous circle or loop of magnetic core material for confining and containing the magnetic flux induced therein. From a magnetic standpoint, the core is a generally continuous magnetic loop. The magnetic flux is thus confined generally proximate the core and within the body where it is implanted. The core 18 is preferably prepared from a wound tape core specimen having an approximately 1 in. inside diameter, a 1.5 in. outside diameter, and being 0.5 in. high. Layers of the magnetic tape of core 18 are unwound from the inside surface until the core thickness is reduced from approximately 6.35 mm to exactly 4.6 mm. The core 18 is then cleaned of any exposed adhesive. To form the primary coil circuit 20, approximately 11 turns of the primary coil wire are passed around the core 18. The entire core 18 and primary windings 20 are then coated with two layers of polyurethane lacquer (not shown). A coating of silicon rubber (not shown), such as 1300T, available from Shinetzu Chemical Co., Ltd., Tokyo, Japan is then applied. The lacquer and silicon coats do not perceptively reduce the tape core flexibility. The secondary coil circuit 22, in one embodiment, has a 140 cm length which should be sufficient for approximately 14 coil turns (having a mean coil diameter of approximately 3 cm.) This allows the secondary coils 20 to be freely wound around the outside of the closed primary-containing intestinal pouch 24, as illustrated in FIG. 1A. The core 18 and primary coil 20 are positioned in the circular pouch 24 in a procedure discussed further herein below. The high permeability core and the unique configuration and cooperation between the pouch and core are operable to confine the magnetic flux into a generally continuous magnetic loop to reduce and prevent flux leakage outside the body.

FIG. 1B is a cross-sectional view of FIG. 1A, showing the core 18 and primary coil 20 sealed in the intestinal pouch 24. For illustrative purposes, the wire leads to the power source 27 and device 29 are not shown.

Wires for the primary coil current 20 are then formed into the double helix structure 14 and coupled through silicon sphere 16 to a coaxial cable 17. Coaxial cable 17 is then coupled to an external power source 27 as discussed below. Secondary coil 22 is coupled to the appropriate appliance or device 29 driven by device 10 to provide power thereto. Additional specifications for transformer device 10 are shown in Table 1 which lists nominal design specifications for devices 10 (Embodiment 1) and 12 (Embodiment 2) at nominal operating temperatures at 37° C. and using a purely resistive load of 5.8 ohms, and in Table 2. which discloses actual specifications as measured during bench and in vitro tests of the devices 10 and 12. All tests were conducted using a purely resistive load of 5.8 ohms.

TABLE 1

Nominal Design Specifications for Embodiments 1 and 2

| | Embodiment 2 (Dual Core Design) | Embodiment 1 (Single Core Design) |
|---|---|---|
| Operating Conditions | | |
| Frequency (kHz) | 90.2 | 14.7 |
| Primary Voltage ($V_{RMS}$) | 13.8 | 12.8 |
| Primary Current ($A_{RMS}$) | 1.86 | 1.96 |
| Secondary Voltage ($V_{RMS}$) | 12 | 12 |
| Secondary Current ($A_{RMS}$) | 2.07 | 2.07 |
| Core Characteristics | | |
| Relative Permeability | 12200 | 23000 |
| Material Type | Type H Ferrite | Square Permalloy |
| Shape | 2-piece cresentic | 80 0.5 mil tape torroid |
| Primary/Secondary Gap (mm) | 3 | NA |
| Transformer Parameters | | |
| Input resistance (Ω) | 0.036 | 0.05 |
| Input inductance (microH) | 0.45 | 0.7 |
| Effective core resistance (Ω) | 256 | 250 |
| Effective core inductance (microH) | 10.7 | 780 |
| Output resistance (Ω) | −.02 | 0.012 |
| Output inductance (microH) | 1.2 | 0.7 |
| Turns Ratio | 10/10 | 11/14 |
| Performance Specifications | | |
| Winding Losses (W) | 0.325 | 0.095 |
| Core Losses (W) | 0.180 | 0.150 |
| Coil-to-Coil Efficiency (%) | 97 | 99 |

(All figures above are given at a nominal operating temperature of 37 C. and using a purely resistive load of 5.8 Ohms.)

TABLE 2

Actual Specifications As Measured During Bench and In Vitro Tests of Embodiments 1 and 2

| | Embodiment 2 (Dual Core Portion Design)* | Embodiment 1 (Single Core Design) |
|---|---|---|
| Physical Characteristics | | |
| Total Mass (g) | 102 | 68 |
| Total Volume (cc) | 27 | 20 |
| Operating Conditions | | |
| Frequency (kHz) | 90.2–95.3 | 13.8–14.7 |
| Primary | | |
| Voltage ($V_{RMS}$) | 13.7 | 12.7 |
| Current ($A_{RMS}$) | 3.12 | 2.23 |
| Phase Angle (degrees) | 50.4 | 22.0 |
| Power (W) | 27.24 | 26.26 |
| Secondary | | |
| Voltage ($V_{RMS}$) | 12.40 | 12.23 |
| Current ($A_{RMS}$) | 2.13 | 2.12 |
| Phase Angle (degrees) | 7.0 | 13.0 |
| Power (W) | 26.21 | 25.26 |
| Coil-to-Coil Efficiency (%) | 96.2 | 97.8 |

TABLE 2-continued

Actual Specifications As Measured During Bench and In Vitro Tests of Embodiments 1 and 2

|  | Embodiment 2 (Dual Core Portion Design)* | Embodiment 1 (Single Core Design) |
| --- | --- | --- |
| Calorimetrically Measured Heat | 0.95 | 0.82 |

*Embodiment 2 figures given at 3 mm primary/secondary gap distance.
(All tests conducted using a purely resistive load of 5.8 Ω on one sample of each type.)

Embodiment 2

Figure 2A:
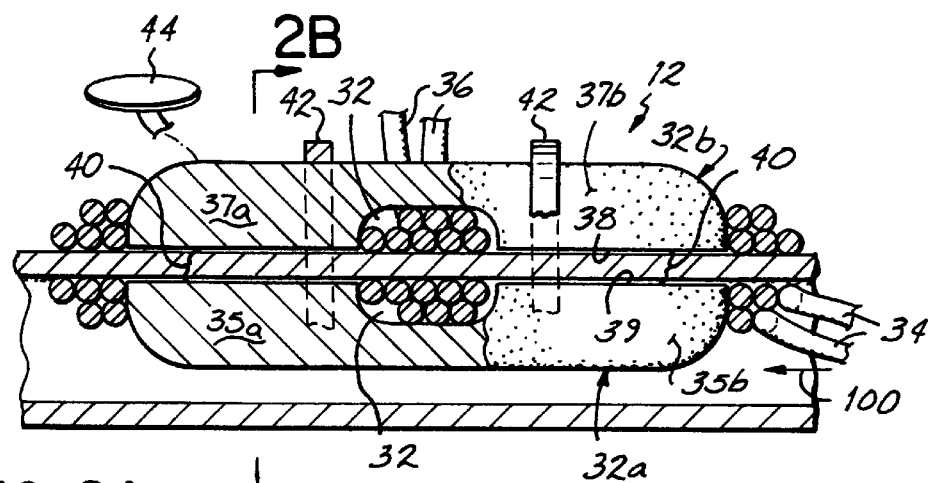
FIGS. 2A and 2B are diagrammatic cross-sectional views of an alternate embodiment of the present invention.
Figure 2B:
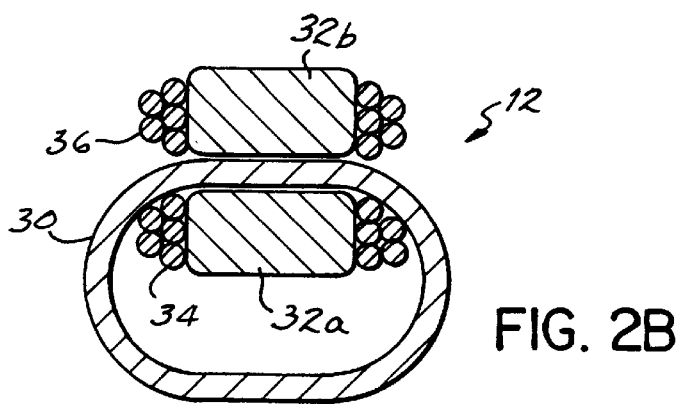

The device 12 illustrated in FIGS. 2A and 2B is shown positioned inside and outside of a straight segment of isolated intestinal pouch 30. Device 12 includes a high permeability magnetic core 32, primary windings 34 around a portion 32a of the core 32, and secondary windings 36 around another portion 32b of the core. Core 32 is a two-part core with an intraluminal (extracorporeal) primary portion 32a and extraluminal (intracorporeal) secondary portion 32b which are generally identical and which are designed for placement, facing each other, inside and outside of the straight segment isolated intestinal pouch 30. The core portions 32a, 32b cooperate to form a generally continuous magnetic loop. Reference numeral 31 designates the inside of the pouch. Core 32 is a crescentic core which is cut and machined from a large torroid of high permeability ferrite material, such as material available from Magnetics, Butler, Pa. The length of core 32 is approximately 6 cm., while its thickness is approximately 1.2 cm. and its width is approximately 1.25 cm. FIG. 2A illustrates the core portions 32a, 32b generally facing each other on either side of the pouch wall for proper magnetic coupling. Core portion 32a has the primary core winding 34 wrapped therearound with a suitable wire as discussed hereinabove. Portion 32a is wound with approximately 10 turns of wire concentrated near the ends of the core. The ends of the primary coils 34 exit from one end of the primary as illustrated in FIG. 2A. The secondary portion of the core 32b is also wrapped with approximately 10 turns of wire to form secondary coil 36. The ends of the coils 36 exit proximate the center of the secondary, as illustrated in FIG. 2A.

As with the core 18 in the device 10 discussed above, core 32 has a shape that is generally circular. Core 32 is not completely solid and includes two separated portions. However, in accordance with one aspect of the invention, core 32 forms a circle or loop of magnetic core material which, from a magnetic perspective, is a generally continuous magnetic loop. In that way, the magnetic flux induced in the core is confined and contained in and proximate the core 32 and within the body in which the core is implanted. This makes the power supply of the invention generally less susceptible to external interference and to the generation of stray magnetic fields outside the body.

The shape of the two core portions 32a, 32b provide each portion with two large faces 38, 39. In that way, when the core portions 32a, 32b are positioned proximate the walls of the intestinal pouch 30, the magnetic circuit contains two air (or tissue) gaps 40. Each of the core portions 32a, 32b are covered in a silicone core encapsulant (not shown). As such, each of the core portions 32a, 32b are separated by approximately 2.5–3 mm of space which is formed by the wall of the pouch 30 plus the thickness of the silicone core encapsulant.

The secondary coil 36 and core portion 32b are preferably fitted with a clasp 42 including a plurality of prongs which will engage the pouch 30 and secure the core portion 32 thereto. An elliptical disk 44 (not shown to scale) is also coupled to core portion 32b for being fixed to the abdominal wall fascia (not shown). The elliptical disk 44 may be made of a bio-compatible material, such as polyester, and serves to attach the device 12 to the ileum and to the abdominal wall so that it does not move around within the abdominal cavity. In one embodiment of the invention, the clasp 42 and disk 44 are made of polyester double-knit fabric which is impregnated with silicone rubber, such as the 1300T available from Shinetzu Chemical Co., Ltd., Tokyo, Japan. Further parameters and additional details for device 12 are set forth in Tables 1 and 2 herein.

Power Supply

Figure 4:
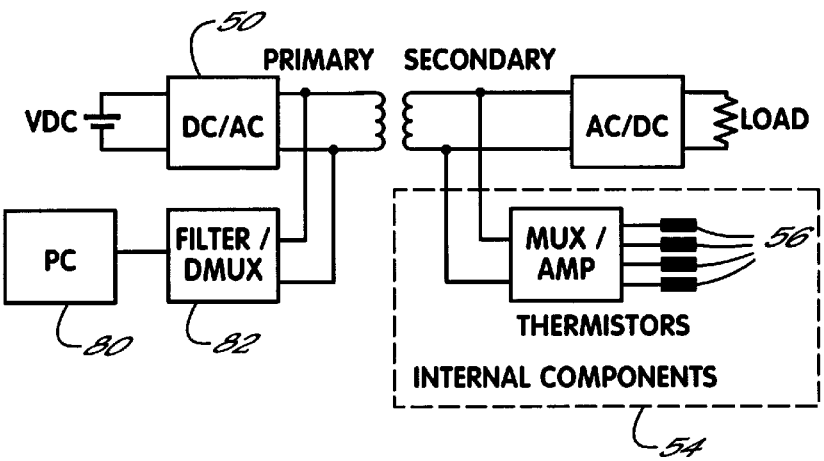
FIG. 4 is a wiring schematic of the present invention.

The transformer devices 10, 12 are components within a complete transintegumental energy transmission system shown schematically in FIG. 4. On the input, or primary side, of the transformer devices, the respective coils are coupled to a DC to AC converter 50. The converter 50 is configured to function in autotuning fashion so that its operational efficiency remains at optimal levels despite varying load conditions. For example, the invention will be able to power various different devices with different load characteristics. The transformer device may interface with a portable rechargeable battery pack VDC which is suitable as the main power supply for the system. On the secondary side of the transformer device, an AC to DC converter 52 is provided for coupling with the implanted device to be powered indicated in FIG. 4 as LOAD. The DC/AC and AC/DC converters should be designed to minimize losses so as to maximize the life of battery VDC and to minimize tissue heating. In one embodiment of the invention, a Series Resonant Converter is utilized for the DC/AC converter 50. A Schottky Bridge Rectifier configuration is suitable for the AC/DC converter 52. Such configurations prove suitable for converters which were tuned to each of the transformer embodiments 10, 12 utilizing a purely resistive load of 5.8 Ohms and a fixed gap distance of 3 mm for the transformer embodiment 12. For such converters, 90.2 kHz was used for the transformer device 12 and 14.7 kHz was used for transformer device 10.

Temperature Monitoring System

In accordance with one aspect of the present invention, the output of the secondary of the transformer devices 10, 12 may be utilized to drive sensing or monitoring devices implanted within the body. Furthermore, additional monitoring and measurement systems might be coupled to the secondary power output to monitor conditions within the body. Specifically, a temperature monitoring system may be utilized to accurately determine body and tissue temperatures around the transformer devices and also the implanted devices. Referring to FIG. 4, one such system 54 is shown utilizing a plurality of thermistors 56 for monitoring tissue temperature. Suitable thermistors are 2500 ohm thermistors available from Yellow Springs Instruments, Inc., of Yellow Springs, Ohio. The temperature processing system 54 is preferably configured on a printed circuit board or rendered in a hybrid or integrated form and embedded in a medical grade elastomer such as the 1300T rubber discussed above. System 54, including the temperature monitoring system and any other additional monitoring systems are coupled to the secondary coil circuit of the transformer device to derive operative power therefrom. Furthermore, as discussed further hereinbelow, data from system 54, including temperature data or other appropriate data, is modulated and superimposed onto the secondary coil circuit and transmitted back across the transformer device to be read externally from the primary coil circuit.

Figure 5:
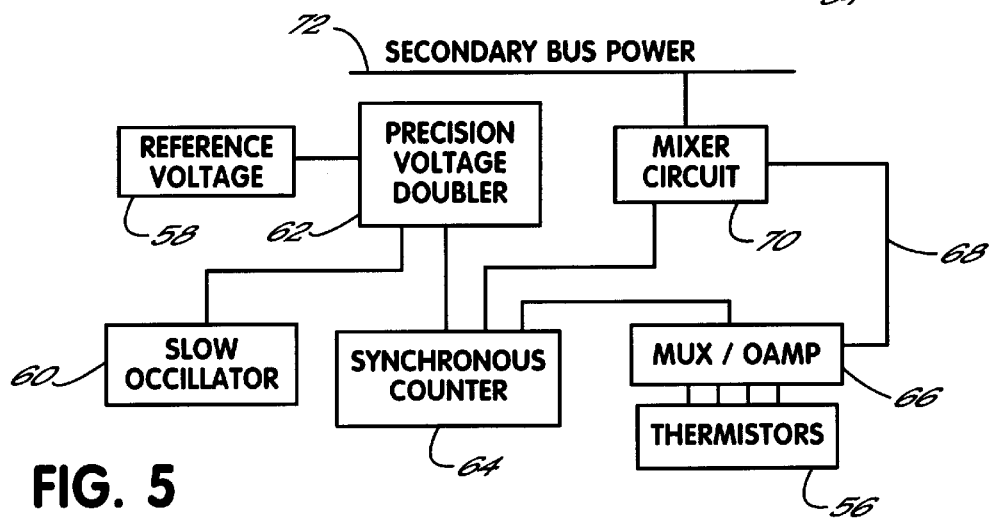
FIG. 5 is a more detailed schematic of an element in FIG. 4.

The temperature measurement from the thermistors 56 is coupled through transducer circuitry to be modulated and superimposed onto the secondary coil circuit. Referring to FIG. 5, circuitry of a transducer circuit coupled to the thermistors 56 is shown. One embodiment of the transducer circuit utilizes a reference voltage 58, slow oscillator 60, precision voltage doubler 62, synchronous 4-bit or other-bit counter 64, and multiplexer/opamp 66, to provide an output on line 68 to a mixer circuit 70. Mixer circuit 70 modulates the transducer output so that it may be superimposed in the secondary coil circuit indicated as secondary power bus 72 in FIG. 5. The transducer circuitry illustrated in FIG. 5 may be powered from the secondary power bus 72, or may be coupled to a disposable battery supply such as Panasonic Inc. Model 2318C.

Figure 6:
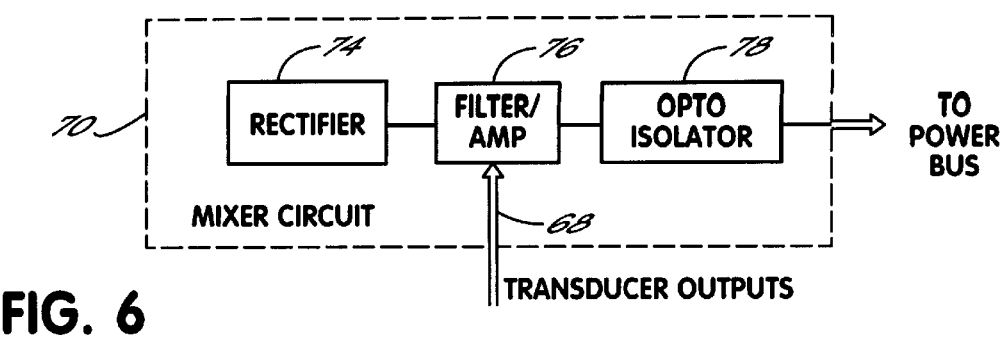
FIG. 6 is a more detailed schematic of an element of FIG. 5.

A more detailed schematic of the mixer circuit 70 is illustrated in FIG. 6. The mixer circuit 70 will include a rectifier 74 if the mixer circuit 70 is powered from the secondary power bus 72. If it is powered from a battery, the rectifier 74 may be eliminated.

The transducer outputs 68 from the transducer circuitry are frequency modulated and passed to a filter/amplifier 76 for eliminating noise and interference. Rectifier 74 powers the active filter 76. Again, if a disposable power supply is utilized, the filtering stage of the filter/amplifier 76 may be eliminated. The filtered transducer outputs then must be mixed or encoded onto the secondary power bus 72 for transmission to the primary coil circuit. To that end, an optoisolator 78 is utilized. A suitable active filter for filter/amplifier circuit 76 is an OP270 Op Amp, whereas a suitable rectifying circuit is an LM340 12-volt regulator. Optoisolator 78 may be a GE 4N35 Optoisolator which is utilized to mix the signal back onto the power bus 72.

Once the transducer signals on the secondary power bus, the signal will pass to the primary coil circuit where it is demodulated and then processed by a processing device, such as a personal computer 80 or a microprocessor (see FIG. 4). On the primary side of the transformer device, a filter/demultiplexer unit 82 is coupled to the primary coil circuit. The filter/demultiplexer unit 82 incorporates a band pass filter which is implemented to eliminate the power line carrier frequency of 14.7 kHz from the transducer output signal. The transducer output signal, which is received outside of the body is then demodulated utilizing a MF5 Universal Monolithic Switch Capacitor Filter, available from National Semiconductor Inc. The frequency signal is then converted to a voltage usable by the computer 80 utilizing an LM2907 Frequency-Voltage Converter. The various frequencies utilized to transmit the sense temperatures will be different for the different transformer devices 10, 12. For example, with the single core device 10, a center frequency of 80 kHz for a temperature of 39° C. is utilized. For the double portion core transformer device 12, a center frequency of 30.3 kHz is used.

It will be readily understood by a person of ordinary skill in the art that while temperature sensing is discussed in detail herein, other systems might also be powered from the secondary power bus 72 of the transformer device, and other measured values might be transferred for outside processing through the primary and secondary coil circuits. Furthermore, this communications link between the primary and secondary coils could be configured in a bidirectional mode so that signals could be transferred both from outside to inside the body (primary to secondary) as well as inside to outside, as disclosed in the Figures.

For device 12, for example, sensitivity of the system is 1112 Hz/C. Linearity is 1% between 35 and 42° C. for each system. The system functions at all secondary coil voltages $\geq 1.7$ V and consumes 0.07 W. The thermistors used were rated as accurate to <0.01° C. Calculated accuracy of the system including processing and transmission was calculated conservatively <0.05° C. This method is chosen rather than use of a separate cable for thermistor leads because of concern that additional entry sites would offer additional sites for infection in the experimental model. Further, it was desirable to develop a method suitable for multichannel monitoring of longer term trials in which power would either be internally expended or exit by a second transformer.

The transformer devices 10, 12 of the present invention are implanted into intestinal sacks or pouches 24, 30 to permit extra- to intra-corporeal power transfer. In one embodiment of the invention, the intestinal pouch is formed as an ileal pouch as discussed in detail below. However, other intestinal sections might be utilized to form the pouch. Preferably, the ileal pouch 24, 30 will be of the Roux-Y type. To form a Roux-Y segment (as shown in FIGS. 7A and 7B), a vascularized segment of the ileum 90, including the mesentery, is isolated and cut at line 92 forming an upstream portion 94 which comes from the gut and a downstream portion 96 which leads to the large intestines. The downstream portion 96 will be formed into an ileostomy attached to the patient's skin at a small stoma (not shown) which will permit wires from the primary to pass there through. The cutaneous stoma is formed in the lower abdominal region. A small slit is formed through muscle tissue and the edge of intestinal pouch 98 is passed through the slit and sewn to the skin.

The arrows 100 depicted in FIG. 7 demonstrate the peristalsis. The edge 102 of the upstream portion 94 is then connected to the extreme downstream portion 104 of the selected segment of ileum 90 so there can be peristaltic flow as shown by arrows 100 from the upstream segment to the downstream segment. The portion from the stoma to this juncture 106 between the upstream segment and the downstream segment forms the pouch 24 or 30 for use in the present invention.

In order to implant the circular loop magnetic core 18, a circular intestinal pouch 24 is formed during implantation as shown in FIG. 1A. In order to do this, an adequate length of defunctionalized intestinal segment 96 is formed into a circular transformer pouch. A desired length of the anti-mesenteric border is opened longitudinally. A proximal portion adjacent the opening was joined to a distal portion stapled by side to side anastomoses. The core or coil assembly 18 is positioned within the segment 96 by carefully closing the longitudinal incision around it with either sutures or end to end anastomotic stapler. This leaves a central hole through the pouch and the core. The wire for the primary winding is extended through the portion 98 upstream end and out the formed stoma. A silicone bulb 16, bonded to the primary wires in the pouch, prevents the wires from moving in and out through the small cutaneous stoma. The secondary wire 22 is freely wound after placement of a single layer omental wrap and passes repeatedly through the mesentery (not depicted). The leads are connected by a silicone insulated solder joint, as shown in FIGS. 3 and 4.

The transformer containing pouch is positioned preferably within the split rectus muscle and interior sheath closed.

The pouch position is maintained by closing the interior fascia and keeping or restoring the opening in the posterior fascia to a size which is too small for the transformer to fall inside but sufficiently generous for mesentery draining loop and omental pedicle.

The transformer 32 shown in FIGS. 2A and 2B is positioned in a somewhat different manner. Again a Roux-Y segment is formed (not shown in these drawings). The intraluminal primary 32a and extraluminal intercorporeal secondary 32b appliances are identical in design for placement facing each other inside and outside a straight segment isolated intestinal pouch. Each has a crescentic core 32 cut and machined from a large toroid of high permeability ferrite and each is wound with ten turns of wire concentrated near the ends of the cores. Wires 34 exit from one end of the primary portion 32a and from the center of the secondary portion 32b. The shape of the two cores provides two large faces so that with intended positioning the magnetic circuit contains two tissue gaps.

As shown in FIGS. 2A and 2B, the primary coil 34 with windings around distal ends 35a and 35b thereof is positioned within the distal end of the pouch. The secondary core portion 32b again with windings 36 around distal ends 37a and 37b is placed positioned exterior of the ileal pouch with core fascia opposite those core fascia of the primary facing each other across the anti-mesenteric wall. Clasps 42 are passed through the mesentery (not depicted) and sutured to hold the secondary portion 32b in position. A generous omental patch 44 is suture-tacked to the aspect of the coil pouch assembly which would face the free peritoneal cavity. The transformer contained pouches are then positioned within the split rectus muscle and the anterior sheath closed. Pouch position is stabilized by suturing the edges of the polyester fixation disk to the anterior fascial margins using the disk to complete the closure. Thermistors or other analytical devices can be fixed as desired.

EXAMPLE

Transformers were placed in each of eight 34–42 kg. mixed breed male dogs. Four received two-piece and four received one-piece loop devices. Through a very small (5 cm) left paramedian incision, a 50 cm. segment of distal ileum was identified, using a laparoscopic videocamera when available to minimize manipulation. The segment was irrigated with normal saline and iodophor antiseptic, divided, and reconnected as a vascularized, internally drained and defunctionalized Roux-Y segment.

Two piece transformers were placed by advancing the primary coil assembly 15 cm into the open proximal end of the intestinal segment. The secondary coil was positioned with core faces opposite those of the primary across the antimesenteric wall. The clasp was passed through the mesentery and sutured.

One-piece loop device placement began by identifying the 10 most proximal cm of the defunctionalized segment for primary lead exit, and the 28 most distal cm for internal drainage of any secretions. The remaining 12 cm was formed into a circular transformer pouch: the central 7 cm of the antimesenteric border was opened longitudinally and the 2.5 cm just proximal to the opening was joined to the 2.5 cm just distal by a stapled side-to-side anastamosis. The core/ coil assembly was positioned by carefully closing the longitudinal incision around it with either sutures or an end-to-end anastomotic stapler. The secondary wire was freely wound (14 turns of about 3 cm diameter, penetrating mesentery with each pass) after placement of a single layer omental wrap and connected by a silicone-insulated solder joint.

Two thermistors were fixed to serosa between turns of the secondary and two placed remotely in the abdominal cavity. The thermistor data processor unit was placed caudal to the incision in a bluntly dissected pocket behind the rectus muscle. A generous omental patch was suture-tacked to the aspect of the coil/pouch assembly which would face the free peritoneal cavity. The transformer-containing pouches were then positioned within the split rectus muscle and anterior sheath closed. Pouch position of the two-piece core was stabilized by suturing the edges of the polyester fixation disc to the anterior fascial margins, using the disc to complete closure. The one-piece core position was maintained by closing anterior fascia and either keeping or restoring the opening in the posterior fascia to a size too small for the transformer to fall inside but sufficiently generous for mesentery, draining loop, and omental pedicle.

An opening is made in the left upper quadrant fascia. In a clinical procedure, a small cutaneous pouch stoma would be formed around the entering primary wires. In this experimental model, due to repeated chewing of primary wires at stomal exits by our otherwise cooperative subjects in preliminary studies, the procedure was altered. Proximal segment end was closed after bringing the primary coaxial cable through a 2.5 cm Witzel tunnel and the primary lead cable was tunneled to a posterior cervical exit site. The abdominal fascia opening was calibrated as is intended for direct stomas, smaller than the retaining sphere to restrict transfer of incidental lead wire traction to the primary appliance. While Witzel tunnels are in effect exteriorized (unlike lines leading to truly intracorporeal devices, they open to epithelized surfaces at both ends) and have functioned well for several months in varied clinical applications, it is emphasized that here they were only used as a specific modification to allow canine evaluation. To allow secondary output monitoring and dissipation in the experimental model, the secondary lead cable was tunneled to a similar exit site.

Maintenance, Power Delivery, and Monitoring

Each animal was allowed to awaken and given free range of his run for at least 48 hours, to allow resolution of any postoperative vasoconstriction that might affect heat dispersion. Then, a tether system with an 8 connector mercury wetted slip ring (available from Mercotac of Carlsbad, Calif., allowed free lying, standing, and 360/free rotation. DC power delivery to the converter was begun at 48 to 96 hours after operation and steadily increased by a ramp funciton designed to achieve a "full power" post rectification DC output of approximately 12.1 V, 2.0 to 2.1 A at 144 hours (6 days) after operation. Input DC voltage at full power was 28 to 28.1 V, with input current varying with transformer function. Input and output voltages and currents, and readings of all four thermistors, were recorded by an on-line 386–33 PC at 5 minute intervals. The animal was disconnected for from 15 to 30 minutes at least once daily for exercise. Primary power was returned (ramp function from 0 voltes) to the pre-disconnection level over 15 minutes. Full power was maintained, except for exercise interruptions, for a minimum of 5.6 and maximum of 11.8 days.

Terminal Observations and Necropsy

Magnetic flux at skin surface and sensitivity of the transformers to contiguous metal objects were assessed under general anesthesia (sodium pentobarbital). Magnetic flux was measured by gauss meter (Model 610, available from Bell Laboratories) at 2 cm intervals over a 10×12 cm abdominal wall grid centered over the coils in two animals of each device group. The greatest measured surface flux and its location were recorded. Then 5 cm thick metal plates, first of aluminum and then of iron, (radius of each ≧5 cm in all directions from central contact point), were repeatedly placed in and removed from contact with that point while rectified secondary circuit current was monitored by digital display (50 mA resolution).

Mechanical security of 3 devices in each group was assessed immediately after a lethal dose of sodium pentobarbital by applying 10 pounds traction for 1 minute to the primary cable a short distance from its entry site and inspecting for gross movement. Tissue containing implanted material was removed in block and tissue carefully dissected to expose and remove coils and temperature monitoring devices. The pouch and surrounding peritoneal cavity were inspected for gross damage. One intact pouch assembly from each device-group was immersed in saline, full power transfer was resumed, and magnetic flux readings taken at multiple points contiguous to coils and to the interspersed tissue. Intestinal wall specimens were taken for histologic examination.

Results

Clinical Observations

Animals ate well and appeared well-nourished, indicating normal gastrointestinal function and metabolic status during the implant, both prior to and during power transfer.

In vitro assessment of coil-to-coil efficiency and of heat production:

Voltages, currents, and phase angles for alternating current through the primary and secondary coils of both transformers are listed in Tables I (nominal) and II (in vitro measured results in one example of each type). The efficiency of the individual transformer tested for each type was 96.2%. This represented a loss of 1.03 and 1.00 W for the dual and single core transformers, respectively. Calorimetry measured during the same test on the same devices measured 0.95 and 0.82 W recovered as heat.

Power transfer In Vivo

Analysis of all recordings taken at nominal full power transfer (2.07 amperes at slightly over 12 volts transmitted to the DC output) for both transformers yielded data listed in Table III. The total system efficiency averaged 75.64% and 80.92% for dual and single cores, respectively. This difference was marginally statistically significant by a t-test on means at p+0.0481 and by a t-test on medians at p=0.0416; tested by Repeated Measures Analysis, p=0.0134.

Tissue Temperature

Thermistors and implanted data processing circuitry functioned satisfactorily throughout the study in four of the experimental subjects, two with each of the device types. Data was analyzed at all data points in which full nominal power was transferred, and in which at least one coil and at least one reference temperature was recorded. There was no statistical difference demonstrated between means of temperature differences for the two designs (p=0.3616 by t-test). None of the over 3000 cumulative sets of temperature data indicated a coil to reference difference of over 1.2/C; there was a single instance in a single subject in which a difference of over 1/C was observed for two consecutive readings (5 minutes apart), and no instance of three consecutive such readings.

Magnetic Flux Leakage

In each of the four animals (two in each group) in which it was measured, the highest magnetic flux level on the abdominal skin surface was over the incision scar center, immediately external to the site of transformer placement. Levels were low and similar at 0.9 and 1.6 Gauss for the dual core and 0.8 and 1.2 Gauss for the single core subjects during full power transmission. Background levels in the same room were measured immediately following cessation of power delivery. The probe was positioned against wall surfaces, floor, ceiling, center of room space, and in contact with the body surface of the examining surgeon and engineer. No background reading was less than 0.3 nor greater than 0.6 Gauss.

Sensitivity To Contiguous Metal Objects

Neither the 5 cm thick plate of aluminum, nor the 5 cm thick plate on structural steel, was accompanied by detectable change in rectified secondary current during full power transmission. With baseline current of 2.10 to 2.15 amperes across a fixed resistive load and sensitivity of monitoring device of 50 mA, maximum undetected attenuation would have been less than 2.5% of transmitted power.

Mechanical Stability

Traction of ≧pounds on primary lead line immediately after euthanasia, sustained for 1 minute in 3 subjects of each design group, did not produce gross movement of the lead. No sign of trauma to the pouch was seen at necropsy immediately following (see below).

Necropsy Findings

All suture and staple lines in coil pouches were intact and there was no indication of infection or of tissue necrosis in any of the subjects. Each of the dual core pouch segments was dilated in the portion proximal to the primary coil (through which lead wires entered)d and in two of them, there was localized collection of mucoid fluid, one in subcutaneous tissue and one intraperitoneally. By contrast, all all single core transformers were free of mucus retention or extravasation. Pouch walls for both transformer types were free from gross or microscopic ulceration or ischemic changes.

CONCLUSIONS

These observations during brief implantation trials supported the postulated advantages of trans-enteric pouch power transformers; that is, compact appliances, harness-free physical security, minimal warming, and especially, minuscule leakage of magnetic flux. The single core device appears suitable as presently used for intermediate term studies, while the pouch for the dual core device assessed would require a modest alteration. The experimental animal model employed was adequate for these and perhaps for somewhat longer trials, but will not be suitable for definitive chronic evaluations.

TABLE 3

In Vivo Test of Implanted Transformer Types A and B

|  | A (Dual Core Design) | B (Single Core Design) |
|---|---|---|
| Operating Conditions | | |
| Primary | | |
| Voltage (V-dc) | 28.060 pm 0.006 | 28.060 pm 0.006 |
| Current (A-dc) | 1.1910 pm 0.0878 | 1.084 pm 0.0401 |
| Power (W) | 33.419 pm 2.4644 | 30.442 pm 1.1307 |
| Secondary | | |
| Voltage (V-dc) | 12.024 pm 0.440 | 12.038 pm 0.164 |
| Current (A-dc) | 2.0708 pm 0.0492 | 2.0702 pm 0.0458 |
| Power (W) | 24.899 pm 1.5044 | 24.921 pm 0.8908 |
| DC-to-DC Efficiency (%) | 75.63 pm 2.74 | 80.92 pm 3.27 |
| Measured Warming (C) | 0.6204 pm 0.2969 | 0.7257 pm 0.1880 |
| Magnetic Flux (peak, Gauss) (background level 0.3–0.6 Gauss) | 0.9, 1.6 | 0.8, 1.2 |
| Observed Power Attenuation (Contacting thick iron plates) | none* | none** |

(All tests conducted using a purely resistive load of 5.8 Ohm.)
*Type A transformer figures given at 3 mm primary/secondary gap distance.
**Equipment resolution of 50 mA monitoring secondary current of approximately 2.1 A.

While the present invention has been illustrated by the description of the embodiments thereof, and while the embodiments have been described in considerable detail, it is not the intention of the applicant to restrict or in any way limit the scope of the appended claims to such detail. Additional advantages and modifications will readily appear to those skilled in the art. Therefore, the invention in its broader aspects is not limited to the specific details representative apparatus and method, and illustrative examples shown and described. Accordingly, departures may be made from such details without departure from the spirit or scope of applicant's general inventive concept.

What is claimed is:

1. Method of implanting an extra- to intra-corporeal power supply within a mammal, comprising:
   positioning at least a portion of a high permeability magnetic core wrapped with a primary coil within an intestinal pouch;
   the core defining a generally continuous magnetic loop for confining magnetic flux proximate the core; and
   establishing a secondary coil around a portion of the core, the secondary coil being positioned exterior to said intestinal pouch and magnetically coupling with said primary coil in the pouch;
   wherein said generally continuous magnetic loop confines the magnetic flux of the supply to reduce flux leakage in the mammal.

2. The method of claim 1 wherein said magnetic core is continuous and has a central opening therein and further comprising:
   forming said intestinal pouch around the core and primary coil to have a central opening corresponding with said central opening of said core; and
   positioning said secondary coil around the core and pouch to extend through said central openings of the core and pouch.

3. The method of claim 1 wherein said entire core is positioned within the intestinal pouch.

4. The method of claim 3 wherein at least a portion of the primary coil extends around opposite ends of the first core portion and wherein at least a portion of the secondary coil extends around opposite ends of the second core portion.

5. The method of claim 1 wherein said core includes first and second portions and the first core portion, including the primary coil, is positioned within the intestinal pouch, the method further comprising:
   placing the second core portion exterior to said intestinal pouch and separated from the first core portion;
   positioning the second core portion adjacent a wall of the pouch for magnetically coupling the core portions together, the first and second core portions positioned for defining the generally continuous magnetic loop for confining magnetic flux proximate the core;
   positioning the secondary coil around the second portion of the core.

6. The method of claim 5 wherein said first and second core portions both have faces and wherein said first and second core portion faces are positioned on opposite sides of a wall of said intestinal pouch separated only by a narrow gap to thereby form said continuous magnetic loop.

7. The method of claim 1 further comprising coupling a source of power to said the primary coil to create a magnetic flux in the core.

8. Method for monitoring conditions inside a mammal using an implanted extra- to intra-corporeal power supply, comprising:
   positioning at least a portion of a high permeability magnetic core wrapped with a primary coil within an intestinal pouch;
   the core defining a generally continuous magnetic loop for confining magnetic flux proximate the core;
   coupling a processing device to the primary coil;
   establishing a secondary coil around a portion of the core, the secondary coil being positioned exterior to said intestinal pouch and magnetically coupling with said primary coil in the pouch;
   coupling a sensing device to the secondary coil;
   generating signals on the secondary coil with the sensing device;
   coupling the signals to the primary coil and processing the signals on the primary coil with the processing device.

9. The method of claim 8 wherein said sensing device includes a thermistor.

10. The method of claim 8 wherein the sensing device generates output signals, the method further comprising modulating the output signals to generate said signals on the secondary coil.

11. An extra- to intra-corporeal power supply system for use within a mammal, comprising:
   a high permeability magnetic core wrapped with a primary coil;
   an intestinal pouch formed from a section of a mammalian intestine and configured for covering a portion of the magnetic core and the primary coil;
   the core configured for defining a generally continuous magnetic loop for confining magnetic flux proximate the core;
   a secondary coil wrapped around a portion of the magnetic core, the secondary coil being positioned adjacent and exterior to said intestinal pouch and magnetically coupled with said primary coil in the pouch;

wherein said generally continuous magnetic loop confines the magnetic flux of the supply to reduce flux leakage in the mammal.

12. The power supply system of claim 11 wherein said magnetic core is continuous and has a central opening therein, said intestinal pouch being formed around the core and primary coil to be generally continuous and to have a central opening corresponding with said central opening of said core, the secondary coil being wrapped around the core and intestinal pouch to extend through said central openings of the core and pouch.

13. The power supply system of claim 11 wherein said entire core is positioned within the intestinal pouch.

14. The power supply system of claim 11 wherein said core includes first and second portions, the first core portion and primary coil being positioned within the intestinal pouch and the second core portion and secondary coil being positioned exterior to said intestinal pouch and separated from the first core portion, the second core portion positioned adjacent a wall of the pouch for magnetically coupling the core portions together to define the generally continuous magnetic loop.

15. The power supply system of claim 14 wherein said first and second core portions both have faces, said first and second core portion faces being positioned on opposite sides of a wall of said intestinal pouch separated only by a narrow gap to thereby form said continuous magnetic loop.

16. The power supply system of claim 14 wherein at least a portion of the primary coil extends around opposite ends of the first core portion and wherein at least a portion of the secondary coil extends around opposite ends of the second core portion.

17. The power supply system of claim 11 further comprising a sensing system coupled to said secondary coil, the sensing system operable for sensing a condition in the mammal and generating signals on said secondary coil in a form receivable by the primary coil for communicating the condition through the intestinal pouch.

18. The power supply system of claim 17 further comprising a processing device coupled to the primary coil for processing the received signals corresponding to the sensed condition.

* * * * *